United States Patent
Thuman

(10) Patent No.: US 10,422,735 B2
(45) Date of Patent: Sep. 24, 2019

(54) FILTER MONITORING IN PNEUMATIC TRANSPORT SYSTEMS

(71) Applicant: Piab AB, Täby (SE)

(72) Inventor: Fredrik Thuman, Österskär (SE)

(73) Assignee: Piab AB, Taby (SE)

( * ) Notice: Subject to any disclaimer, the term of this patent is extended or adjusted under 35 U.S.C. 154(b) by 0 days.

(21) Appl. No.: 15/983,636

(22) Filed: May 18, 2018

(65) Prior Publication Data
US 2018/0340877 A1 Nov. 29, 2018

(30) Foreign Application Priority Data
May 23, 2017 (EP) .................................. 17172335

(51) Int. Cl.
| B65G 53/66 | (2006.01) |
| G01N 15/08 | (2006.01) |
| B65G 51/00 | (2006.01) |
| B65G 43/02 | (2006.01) |
| B65G 53/60 | (2006.01) |

(52) U.S. Cl.
CPC ......... *G01N 15/0826* (2013.01); *B65G 43/02* (2013.01); *B65G 51/00* (2013.01); *B65G 53/60* (2013.01); *B65G 53/66* (2013.01); *B65G 2203/0266* (2013.01); *B65G 2207/40* (2013.01); *G01N 2015/084* (2013.01)

(58) Field of Classification Search
CPC ........ B65G 53/60; B65G 43/02; B65G 53/24; B65G 53/26; B65G 53/66
USPC .................. 406/15, 151, 152, 153, 171, 172
See application file for complete search history.

(56) References Cited

U.S. PATENT DOCUMENTS

| 3,069,205 A | * | 12/1962 | McIver | ................... | B65G 53/00 |
| | | | | | 406/105 |
| 3,186,770 A | | 6/1965 | O'Neal | | |
| 3,898,018 A | * | 8/1975 | Weis | ......................... | F04F 1/06 |
| | | | | | 417/118 |
| 4,247,227 A | * | 1/1981 | Gohler | ................... | B65G 53/60 |
| | | | | | 406/146 |

(Continued)

FOREIGN PATENT DOCUMENTS

| CA | 2 852 703 A1 | 4/2013 |
| DE | 200 20 587 U1 | 2/2001 |

(Continued)

OTHER PUBLICATIONS

The extended European search report for corresponding EP Patent App. No. 17172335.6 dated Nov. 29, 2017.

*Primary Examiner* — Joseph A Dillon, Jr.
(74) *Attorney, Agent, or Firm* — Renner, Otto, Boisselle & Sklar, LLP

(57) ABSTRACT

A pneumatic transport system (10), comprising at least one material transport carrier for transporting a pneumatic transportable material (M) in the pneumatic system (10) by means of a pneumatic device (1a) adapted to operate with negative pressure on the material transport carrier to transport the pneumatic transportable material (M) in the pneumatic system (10) comprising one or more tubes (13) forming a continuous transport path (CL), wherein a pressure-drop monitoring element (3a) is provided and adapted to monitor filter performance of a separating filter (16) provided in the transport path (CL) and adapted to separate the material transport carrier and the transportable material (M) in the transport path (CL).

11 Claims, 2 Drawing Sheets

(56) References Cited

U.S. PATENT DOCUMENTS

| | | | | |
|---|---|---|---|---|
| 7,488,141 | B2* | 2/2009 | Bivens | B01F 15/00123 |
| | | | | 406/93 |
| 8,967,919 | B2* | 3/2015 | Yaluris | C10G 11/18 |
| | | | | 406/50 |
| 9,611,106 | B2* | 4/2017 | Tell | B65G 53/24 |
| 9,637,320 | B2* | 5/2017 | Moretto | B65G 43/08 |
| 9,637,325 | B2* | 5/2017 | Albin | C10G 11/18 |
| 10,112,333 | B2* | 10/2018 | Thorn | A23P 30/20 |
| 2014/0255110 | A1* | 9/2014 | Albin | C10G 11/18 |
| | | | | 406/145 |
| 2016/0272438 | A1* | 9/2016 | Brewster | B65G 53/66 |
| 2016/0347557 | A1* | 12/2016 | Tell | B65G 53/24 |

FOREIGN PATENT DOCUMENTS

| | | |
|---|---|---|
| EP | 0 526 808 A1 | 2/1993 |
| GB | 2 002 463 A | 2/1979 |
| JP | H04 361922 A | 12/1992 |
| JP | 2000 255776 A | 9/2000 |
| JP | 2002 167041 A | 6/2002 |
| JP | 2012 086935 A | 5/2012 |

* cited by examiner

FILTER MONITORING IN PNEUMATIC TRANSPORT SYSTEMS

RELATED APPLICATION

This application claims priority of European Application No. 17172335.6 filed May 23, 2017, which is hereby incorporated herein by reference.

FIELD

The present disclosure relates generally to pneumatic transport systems. More specifically, the present disclosure relates to filter monitoring in pneumatic transport systems such as in vacuum conveying systems.

BACKGROUND

Pneumatic transport systems are well-known for the transport of pneumatic transportable material between, for example, a first location and a second destination of a plurality of interconnected pipes. A typical pneumatic transport system includes a number of pneumatic pipes interconnected to a conveying line such as a pipe-line to transport pneumatically transportable material therein. A material transport carrier for instance a fluid such as air flowing in the pipe-line is used as a carrier for transporting the pneumatic transportable material within the pipeline. Thus, the pneumatic transport system transports material under fluid pressure, being positive, negative or vacuum pressure. Often vacuum is used as conveyor in these pneumatic transport systems and they are therefore sometimes simply referred to as "vacuum conveying".

Within pneumatic transport systems, such as vacuum conveying systems, one or more filters are used to separate conveyed material and the material transport carrier. Herein, this disclosure these filters are referred to as "separating filters".

Typically, the separating filters used in the described transport systems are essential to obtain over time lasting functionality and performance in the transport system. During operation, the one or more separating filter(s) will be contaminated and typically over time an undesirable pressure drop over the filter will build up typically with a decreasing transport capacity as a result. Typically, some kind of conventional filter cleaning system is provided.

A pressure drop over the one or more separating filter(s) will build up as a result of the filter(s) being used over time and will typically cause a negative effect on the performance/function in the transport system. Typically the increasing pressure drop over the filter is because of particles of a substance (of a material) entering a structure or sticking to a surface of the separating filter and not being removed by the conventional filter cleaning system. Lack of replacement or at least proper maintenance such as cleaning of the separating filter can in worst case even result in a broken separating filter. If the separating filter breaks, the transported material, substance will for instance be blown out through an exhaust port of an ejector and contaminate the ambient environment. In the case of handling a hazardous material containing hazardous substances this can even be fatal for the operator.

Until now, none of the above problems related to pneumatic transport systems and related to improper maintenance of separating filters in such transport systems have been properly addressed according to our best knowledge.

SUMMARY

An object of the present invention is to monitor filter performance of a separating filter in a vacuum conveying system in an improved way compared to conventional technology and methods used.

According to a first aspect, filter performance is monitored, in particular a pressure drop over the separating filter is monitored, which makes it possible to take actions to reduce this pressure drop to maintain capacity requirement over time.

According to a first embodiment of the disclosure, there is provided a pneumatic transport system. The pneumatic transport system comprises at least one material transport carrier for instance a fluid for transporting a pneumatic transportable material in the pneumatic system by means of a pneumatic device adapted to operate with negative pressure on the material transport carrier to transport the pneumatic transportable material in the pneumatic system comprising one or more tubes forming a continuous transport path. A pressure-drop monitoring element is provided and adapted to monitor filter performance of a separating filter. The separating filter is provided in the transport path and adapted to separate the material transport carrier and the transportable material in the transport path.

According to one definition, the term "material transport carrier" is capable to transport or convey transportable material in a pneumatic system. The material transport carrier can be a fluid such as air, nitrogen or any other suitable agent that can be used at least in a vacuum conveying system, or a similar conveying system using positive pressure.

According to one aspect of the present disclosure, the pressure-drop monitoring element is a pressure sensor and typically adapted to measure and capture data of an initial negative pressure behaviour.

According to one aspect of the present disclosure, a controller connectable to and adapted to communicate with the pressure sensor is adapted to collect and store data in a store.

Typically, the pneumatic device is an ejector driven by pressurized air and the pneumatic transport system is a conveying system using a carrier fluid having negative pressure.

Typically, the pneumatic transport system is a conveying system using air of vacuum pressure as the transport carrier fluid. Both also other fluids such as nitrogen can be used instead.

Typically, according to one embodiment, including the aspects of the first embodiment, the controller is adapted to take action, such as automated filter cleaning, due to a particular measured too high pressure drop over the one or more separating filter(s). An advantage with this embodiment is that it will monitor and take actions to reduce this too high filter drop(s) to maintain capacity requirement over time.

Alternatively, according to one embodiment, including the aspects of the first embodiment, the controller is adapted to automatically stop a potential dangerous operation of the transport system due to a particular too low, or essentially missing measured pressure drop over the one or more separating filter(s). An advantage with this embodiment is that it can be used to stop a potential dangerous operation due to an emergency stop action triggered by the too low, or essentially missing pressure drop in the event a separating filter is being damaged.

Herein this disclosure, the term "pneumatic transportable material" is related to any material that can be transported by means of a fluid of negative or positive pressure, such as air or nitrogen of negative or positive pressure.

Herein this disclosure, the term "fluid" includes air, or nitrogen, but is not limited to these fluids.

Herein this disclosure, the term "pneumatic device" is typically an ejector-pump, or an electric vacuum pump but is not limited to these.

BRIEF DESCRIPTION OF THE DRAWINGS

For a more complete understanding of the present disclosure and further advantages thereof, reference is now made to the following detailed description taken in conjunction with the drawings in which.

DETAILED DESCRIPTION

Reference will now be made to the accompanying drawings, which are intended to at least assist in illustrating the various pertinent features of the presented inventions. In this regard, the following description is presented for purposes of illustration and description. Furthermore, the description is not intended to limit the disclosed embodiments of the inventions to the forms disclosed herein. Consequently, variations and modifications commensurate with the following teachings, and skill and knowledge of the relevant art, are within the scope of the presented inventions.

Figure 1:
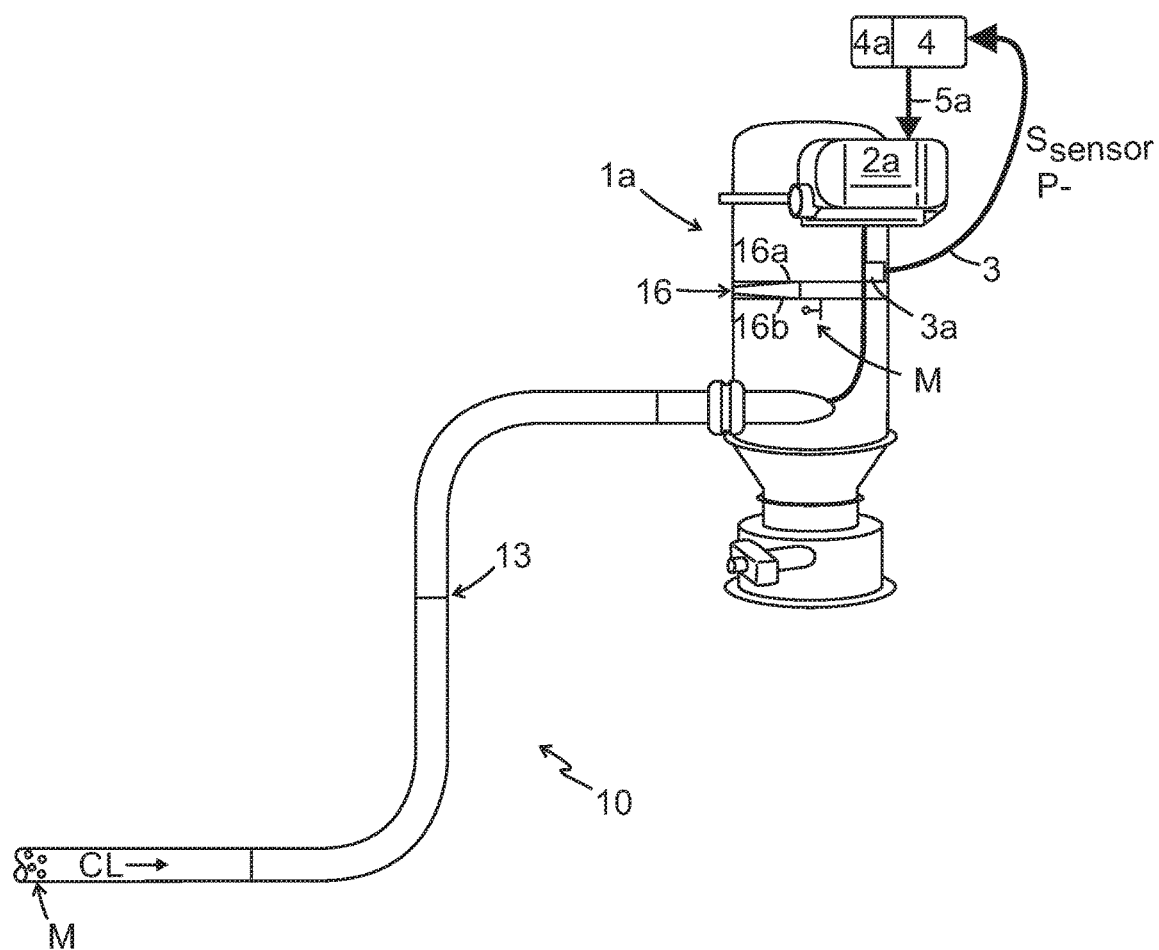
FIG. 1 illustrates one embodiment of a pneumatic transport system according to the invention, comprising a separating filter, a pressure sensor and a controller for filter monitoring.

Now is referred to FIG. 1, which illustrates one embodiment of a pneumatic transport system 10 according to the invention. The pneumatic transport system 10 comprises at least one pneumatic device 1a, herein an ejector (but can alternatively be another type of vacuum pump such as an electrical vacuum pump), for transporting a pneumatic transportable material M in the pneumatic system 10 by means of a carrier fluid, such as a fluid having negative pressure $P^-$, for instance air of vacuum pressure, for transporting the pneumatic transportable material M. The ejector 1a provides a force (see direction of flow in conveying line CL illustrated by an arrow) affecting the carrier fluid, such as air, flowing in the pipes to transport the pneumatic transportable material within the pipes 13. Thus, the pneumatic transport system 10 transports material under fluid pressure or vacuum. Herein, negative pressure, in particular vacuum is provided by the ejector 1a. The pneumatic transportable material M is shown just before it is transported in the pneumatic transport system 10.

The pneumatic transport system 10 typically comprises a plurality of interconnected pipes 13. The pipes 13 may as an example, but not limited there to, be circular in cross-section. The pipes 13 can be made of stainless-steel for instance, or any other suitable material depending on application, together forming a continuous pneumatic transport path CL, sometimes also referred to as a conveying line, for transporting the pneumatic transportable material M. A pressure-drop monitoring element 3a is provided on a clean side 16a of a separating filter 16 and is adapted to monitor filter performance of the separating filter 16 provided in the continuous transport path CL.

Herein, this disclosure "clean side" means the side of the separating filter that is not contaminated with the transported material M.

Herein, this disclosure the terms "transportable" and "transported" material are both used depending on where the material M is located. The term "transported" indicates the location of the transported material at the separating filter 16.

The separating filter 16 is provided and adapted to separate the carrier fluid and the transportable material M in the transport path CL at the ejector 1a. One or more (even though only one is shown in FIG. 1) separating filters 16 can be mounted. In operation, the separating filter 16 will be contaminated (typically on the side 16b opposite to the clean side 16a) and over time of operation an undesirable pressure drop over the separating filter 16 will build up over time with a decreasing capacity over time as a result.

Typically, the pressure-drop monitoring element 3a is a vacuum pressure sensor, if the carrier fluid is air of vacuum pressure, which is connected to the conveying line(s) CL and adapted to sense the system pressure $P^-$. Typically, the vacuum pressure sensor 3a generates a sensor signal $S_{sensor}$ indicative of a particular negative system pressure $P^-$ on the clean side 16a of the separating filter 16. The vacuum pressure sensor 3a can be more or less sophisticated able also to capturing data in addition to monitoring data.

In operation, filter performance of the separating filter 16 is monitored, in particular a pressure drop over the separating filter 16 is monitored, and captured, which makes it possible to take actions to reduce this pressure drop to maintain capacity requirement over time. The vacuum pressure $P^-$ on the clean side 16a of the separating filter 16 is measured, collected and stored over a time frame.

A controller 4 adapted to control including to monitor and to take actions to reduce pressure-drop of the separating filter 16 is connectable to and adapted to communicate via a communication line 3 with the pressure sensor 3a and is furthermore is adapted to collect and store data in a store 4a, which is typically part of the controller 4 or part of the sensor 3a.

The controller 4 is adapted to take action, such as providing automated filter cleaning, due to a particular measured too high pressure drop over the separating filter 16. An advantage with this is that the controller 4 will monitor and take actions to reduce this too high pressure drop over the separating filter to maintain capacity requirement over time. This can be provided by the controller 4 signaling 5a to a filter cleaner unit 2a to clean the filter 16.

Alternatively, or in addition to the above, the controller 4 is adapted to automatically stop a potential dangerous operation of the transport system 10 due to a particular too low measured pressure drop over the filter 16 possibly indicating hole in filter 16. An advantage with this is that it can be used to stop a potential dangerous operation due to an emergency stop action triggered by the essentially missing pressure drop in the event a filter is being damaged.

Figure 2A:
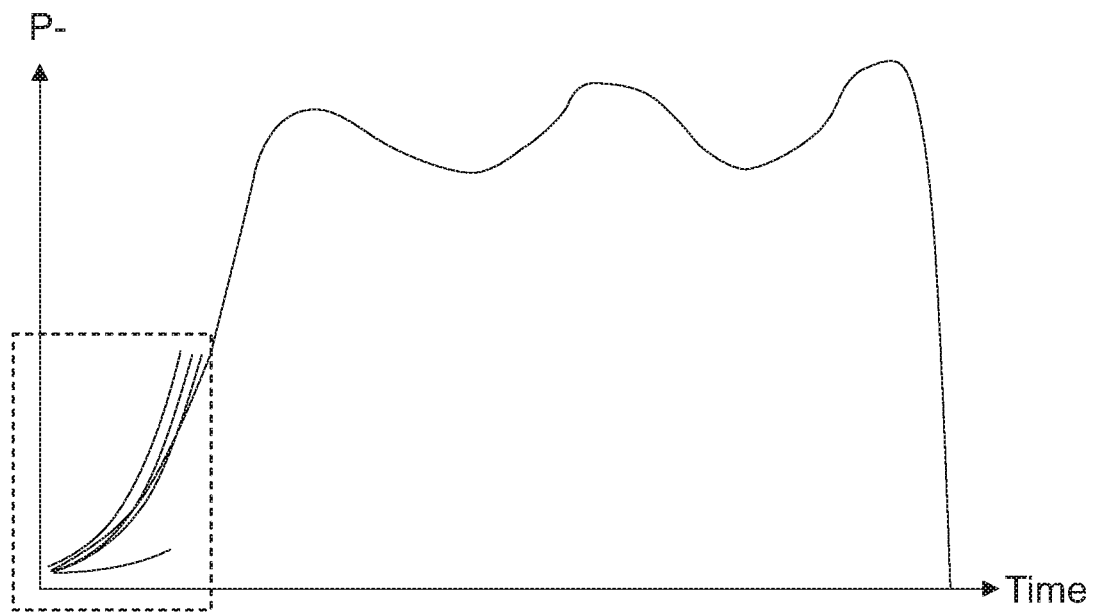
FIG. 2A illustrates a graph of vacuum system pressure vs. time for different measured pressure drops over a separating filter.
Figure 2B:
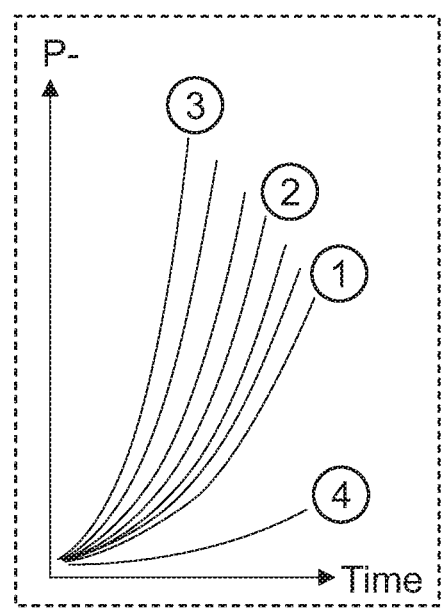
FIG. 2B is an enlargement of the first part of the graph illustrated in FIG. 2A.

Now is referred also to FIGS. 2A and B. FIG. 2A illustrates a whole graph of vacuum system pressure vs. time for different measured pressure drops over a separating filter; and FIG. 2B is an enlargement of the first part of the graph illustrated in FIG. 2A. Mainly is referred to FIG. 2B, since this figure illustrates the most relevant part of the whole graph for explaining the invention.

According to an example, the vacuum sensor 3*a* will be used to collect data of an initial vacuum behavior.

The vacuum level P⁻ on the clean side 16*a* of the filter 16*a* is measured by means of the pressure sensor 3*a* and collected over a certain time frame. The data will be stored and an average initial vacuum characteristic (a graph) of the transport system 10 will be created from a defined number of cycles, say 1-5 cycles. The data collected, which is typically collected by the controller 4 and stored in the store 4*a* into a software, is used to set up a start-up graph, denoted "1" as illustrated in FIG. 2B describing the total initial pressure drop characteristics of the application including the initial pressure drop "1" over the filter 16. This initial pressure drop "1" (see FIG. 2B) will then be used to compare later graphs "2", or "3" to determine the increasing pressure drop over the filter 16. All succeeding cycles, succeeding to the initial pressure drop, as indicated by "1", will be compared to this average start up graph, "1". A limited part of the complete cycle (as illustrated in FIG. 2A) will be used for comparison (as illustrated in FIG. 2A). This limited part as illustrated in FIG. 2A will be defined so that the conveyed material M in the transport system 10 will have no impact.

Based on the information provided from the comparison, a number of measurements can be conducted in order to minimize pressure drop over separating filter 16 by taking an action to reduce pressure drop over the separating filter 16. Example of action taken is a filter cleaning procedure to reduce pressure drop over the separating filter 16.

The filter cleaning process can be repeated at a certain pressure drop level (see "2" in FIG. 2B). For instance, if the pressure drop increases beyond this level (see "2" in FIG. 2B) the filter 16 needs to be automatically cleaned, or alternatively manually disassembled and cleaned, to reduce the filter drop. After a given number of cleaning cycles made, reaching the maximum pressure drop (see "3" in FIG. 2B), used filters need to be replaced with new ones.

If a leakage should occur in the conveyor line CL, the characteristics (graph) will differ from the average characteristics (graph) in an opposite way (see "4" in FIG. 2B) compared to "1", "2" or "3", namely in that the vacuum (or negative pressure) will not build up because of the vacuum flow is directed through an unknown opening towards the ejector 1*a*. This opening will probably consist of a broken filter 16 or a broken bottom valve (not shown). In this case both deviations are severe and will typically result in an emergency stop operation of the transport system 10. This emergency stop operation can be provided by means of the controller 4.

Moreover, the invention can be used also to stop a potential dangerous operation due to the emergency stop action expedient by the missing pressure drop in the event of a filter being damaged.

With this invention, the user of the vacuum conveying system will gain a number of benefits. The most important one is the safety created from the automated emergency stop operation in the event of a filter being damaged. This can prevent human injury because of the prevention of dust of potential hazardous particles in the ambient air being avoided.

Because of the repeated filter cleaning that automatically, or manually, will be conducted repeatedly, the capacity of the conveyed material M can be maintained for an extended period of time compared to a conventional system without this invention. The event of cleaning or changing filters proposed by the system based on the measures and comparison by the software will save a lot of time that were used before in trouble shooting the root cause of the decreasing capacity.

In all embodiments and examples the pneumatic device 1*a* can instead of a fluid driven ejector be an electric driven vacuum-pump.

The foregoing description of the presented inventions has been presented for purposes of illustration and description. Furthermore, the description is not intended to limit the inventions to the forms disclosed herein. Consequently, variations and modifications commensurate with the above teachings, and skill and knowledge of the relevant art, are within the scope of the presented inventions. The embodiments described hereinabove are further intended to explain modes known of practicing the inventions and to enable others skilled in the art to utilize the inventions in such or other embodiments and with various modifications required by the particular application(s) or use(s) of the presented inventions.

What is claimed is:

1. A pneumatic transport system, comprising:
   a pneumatic device configured to operate with negative pressure on at least one material transport carrier fluid for transporting a pneumatic transportable material in the pneumatic transport system to transport in turn a pneumatic transportable material in the pneumatic transport system, the pneumatic device including one or more tubes forming a continuous transport path,
   a separating filter in the continuous transport path, the separating filter being configured to separate the material transport carrier fluid and the transportable material in the transport path,
   a pressure-drop monitoring element for sensing initial pressure drop on the clean side of the separating filter during a start-up period of the system, and
   a controller configured to monitor performance of the separating filter by comparing initial pressure drops sensed by the pressure-drop monitoring element over different start-up periods of the system.

2. The pneumatic transport system according to claim 1, wherein the pneumatic device includes an ejector driven by pressurized air and the pneumatic transport system is a conveying system using a material transport carrier fluid having negative pressure.

3. The pneumatic transport system according to claim 1, wherein the pneumatic device includes an ejector driven by pressurized air and the pneumatic transport system is a conveying system using air having vacuum pressure.

4. The pneumatic transport system according to claim 1, wherein the pressure-drop monitoring element is a pressure sensor adapted to measure and capture data of an initial negative pressure behaviour.

5. The pneumatic transport system according to claim 4, wherein the pressure sensor is a vacuum sensor.

6. The pneumatic transport system according to claim 1, wherein the controller is adapted to collect and store data, obtained by the presure-drop monitoring element in a store.

7. The pneumatic transport system according to claim 6, wherein the controller is adapted to effect automated filter cleaning when the initial pressure drop on the clean side of the separating filter during the start-up period of the system increases by a prescribed amount.

8. The pneumatic transport system according to claim 6, wherein the controller is adapted to indicate manual filter cleaning, or change of filter when the initial pressure drop on the clean side of the separating filter during the start-up period of the system increases by a prescribed amount.

9. The pneumatic transport system according to claim 6, wherein the controller is adapted to automatically stop a potential dangerous operation of the transport system when the initial pressure drop on the clean side of the separating filter during the start-up period is less than a prescribed amount.

10. The pneumatic transport system according to claim 9, wherein the controller is adapted to emergency stop a potential dangerous operation of the transport system when the initial pressure drop on the clean side of the separating filter during the start-up period is less than a prescribed amount.

11. The pneumatic transport system according to claim 1, wherein the pneumatic device includes an electric vacuum pump and the pneumatic transport system is a conveying system using a material transport carrier fluid having negative pressure.

\* \* \* \* \*